US00RE47787E

(19) United States
(12) Reissued Patent
Sturm et al.

(10) Patent Number: US RE47,787 E
(45) Date of Reissued Patent: Dec. 31, 2019

(54) PROCESS FOR PREPARING CEFTAROLINE FOSAMIL

(71) Applicant: SANDOZ AG, Basel (CH)

(72) Inventors: Hubert Sturm, Innsbruck (AT); Josef Wieser, Polling (AT)

(73) Assignee: Sandoz AG, Basel (CH)

(21) Appl. No.: 16/058,177

(22) Filed: Aug. 8, 2018

Related U.S. Patent Documents

Reissue of:
(64) Patent No.: 9,481,698
Issued: Nov. 1, 2016
Appl. No.: 14/436,493
PCT Filed: Sep. 27, 2013
PCT No.: PCT/EP2013/070200
§ 371 (c)(1),
(2) Date: Apr. 17, 2015
PCT Pub. No.: WO2014/060202
PCT Pub. Date: Apr. 24, 2014

(30) Foreign Application Priority Data

Oct. 19, 2012 (EP) ..... 12189300

(51) Int. Cl.
*C07F 9/6561* (2006.01)
*C07F 9/6539* (2006.01)

(52) U.S. Cl.
CPC ..... *C07F 9/65613* (2013.01); *C07F 9/65397* (2013.01); *C07F 9/65615* (2013.01)

(58) Field of Classification Search
CPC ..... C07F 9/65613; C07F 9/65397; C07F 9/65615
See application file for complete search history.

(56) References Cited

U.S. PATENT DOCUMENTS 3,701,775 A * 10/1972 Berges et al. ..... C07D 501/20 540/230
5,827,845 A * 10/1998 Shiokawa ..... C07D 501/00 514/206
6,417,175 B1 * 7/2002 Ishikawa et al. .... C07D 501/00 514/80

FOREIGN PATENT DOCUMENTS

EP 1043327 A1 * 10/2000 ..... C07D 501/00
EP 1310502 A1 * 5/2003 ..... A61K 31/675
JP 2003 300985 A1 10/2003
WO 2010/025328 3/2010
WO 2014/096176 A1 6/2014

OTHER PUBLICATIONS

Cation/Anion List. Arkansas State University Department of Chemistry and Physics. (2010). Web. <https://web.archive.org/web/20101110165722/http://myweb.astate.edu/md raganj/cationanion.html>.*

Byrn, Stephen. Solid-State Chemistry of Drugs, 2nd Ed. (1999), Ch. 11 Hydrates and Solvates, 233-247.*

Morissette, Sherry. Adv. Drug Delivery Rev. 2004, 56, 275-300.*

Rouhi, A. Maureen. Chem. & Eng. News, (2003), 81(8), 32-35.*

Ishikawa, Tak-599, a novel n-phosphono type prodrug of anit-mrsa cephalosporin T-91825: synthesis, physicochemical and pharmacological properties, Biorg. Med. Chem. 11 (2003) pp. 2427-2437.

International Search Report issued in PCT/EP2013/070200, Apr. 12, 2013, pp. 1-4.

Caira, "Crystallie Polymorphism of Organic Compounds," Topics in current chemistry, Springer, Berlin, De, vol. 198, Jan. 1, 1998, pp. 164-208.

Nternational Search Report Issued in PCT/EP2013/077350, Feb. 19, 2014, pp. 1-2.

Copending U.S. Appl. No. 14/653,122, filed Jun. 27, 2015.

* cited by examiner

*Primary Examiner* — Alan D Diamond
(74) *Attorney, Agent, or Firm* — Luedeka Neely Group, P.C.

(57) ABSTRACT

The present invention relates to a novel process for preparing ceftaroline fosamil as well as to intermediates of this process.

12 Claims, No Drawings

PROCESS FOR PREPARING CEFTAROLINE FOSAMIL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention relates to a novel process for preparing ceftaroline fosamil as well as to intermediates of this process.

BACKGROUND OF THE INVENTION

Ceftaroline fosamil ((6R,7R)-7-[(2Z)-2-ethoxyimino-2-[5-(phosphonoamino)-1,2,4-thiadiazol-3-yl]acetyl]amino]-3-[4-(1-methylpyridin-1-ium-4-yl)-1,3-thiazol-2-yl]sulfanyl]-8-oxo-5-thia-1-azabicyclo[4.2.0]oct-2-ene-2-carboxylate; Teflaro) is a cephalosporin antibiotic which is active against methicillin-resistant Staphylococcus aureus and Gram-positive bacteria. It has the general formula

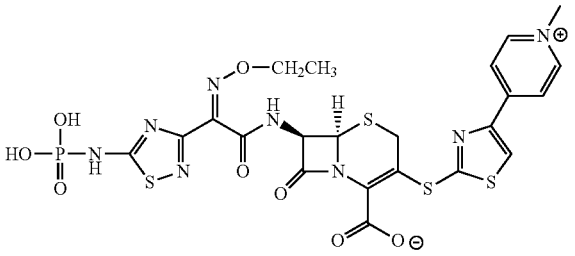

whereby the compound is generally provided in the form of its acetic acid solvate.

EP-A-1 043 327 discusses certain phosphonocephem derivatives:

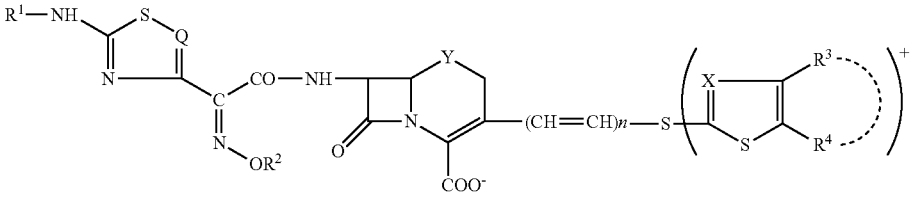

Salts of these compounds are also disclosed.

EP-A-1 310 502 discloses a process for preparing ceftaroline fosamil which includes the following reaction step.

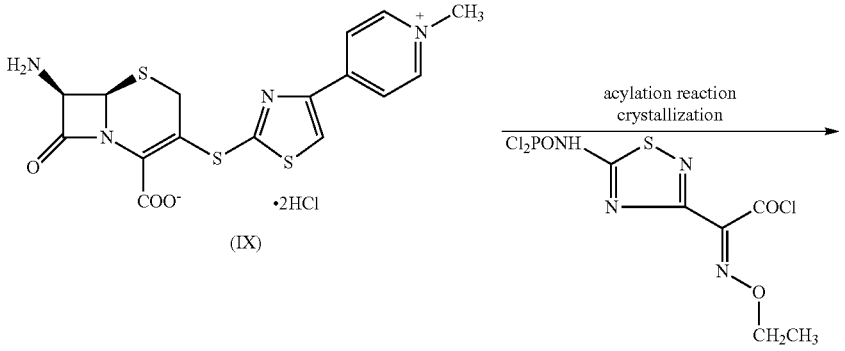

(IX)

(X)

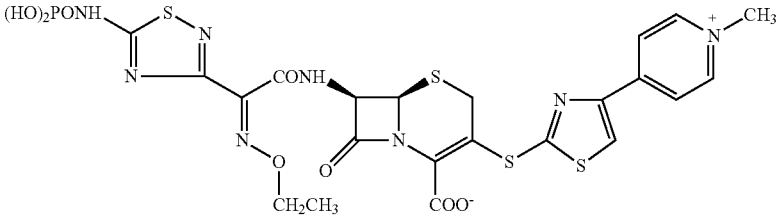

(Ia)

Scavengers such as certain alkali metal salts, tertiary amines, and alkylene oxides can be present in this step.

It was an object of the present invention to provide an improved process for producing ceftaroline fosamil which requires less reaction steps. It was a further object of the present invention to provide an improved process for producing ceftaroline fosamil which results in a lower formation of by-products.

SUMMARY OF THE INVENTION

The present invention relates to a compound having the formula (1)

(1)

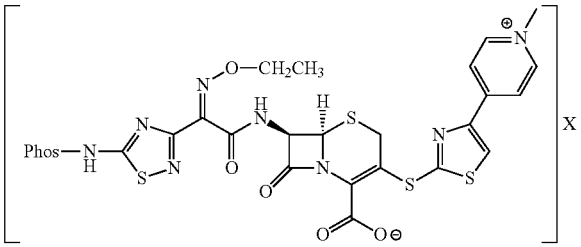

wherein

Phos is a phosphate group; and

X is a cation selected from the group consisting of an imidazolium cation which can be optionally substituted by one or more $C_{1-6}$ alkyl groups and a magnesium cation.

The compound can be provided in the form of a pharmaceutically acceptable solvate.

This compound can be used for the preparation of ceftaroline fosamil.

The present invention also relates to a process comprising the steps of:

(i) reacting a compound having the formula (2) or a salt thereof (2)

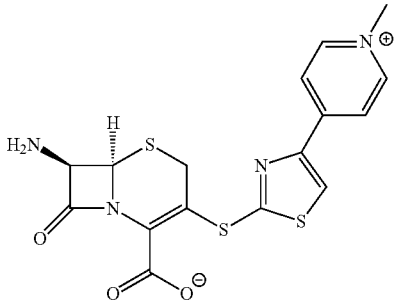

with a compound having the formula (3)

(3)

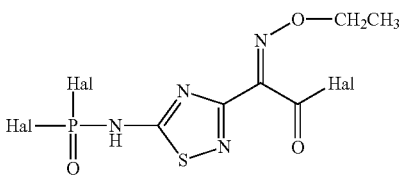

wherein Hal is a halogen; and (ii) adding a reagent selected from the group consisting of a magnesium salt, and an imidazole which can be optionally substituted by one or more $C_{1-6}$ alkyl groups;

to provide a compound having the formula (1)

(1)

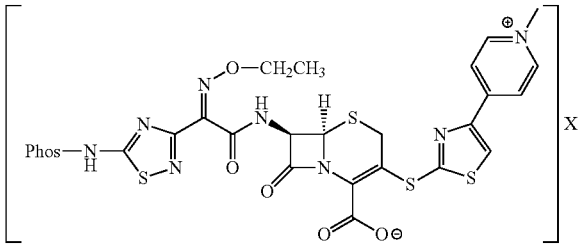

wherein

Phos is a phosphate group; and

X is a cation selected from the group consisting of an imidazolium cation which can be optionally substituted by one or more $C_{1-6}$ alkyl groups and a magnesium cation.

The present invention also refers to a process comprising the steps of:

(a) reacting a compound having the formula (2) or a salt thereof (2)

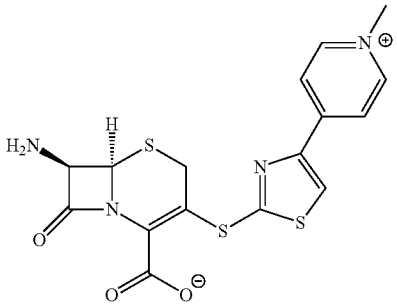

with a silane to provide a compound having the formula (5)

(5)

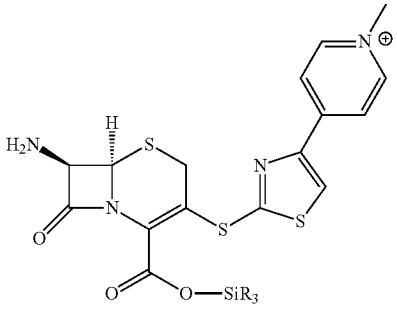

wherein R is independently selected from a $C_{1-6}$ alkyl group;

(b) reacting the compound having the formula (5) with a compound having the formula (3)

(3)

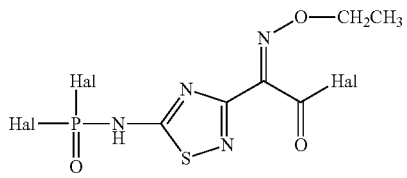

wherein Hal is a halogen; and (c) removing the silyl group —$SiR_3$ from the resultant compound; and (d) adding a reagent selected from the group consisting of a magnesium salt, and an imidazole which can be optionally substituted by one or more $C_{1-6}$ alkyl groups; to provide a compound having the formula (1)

(1)

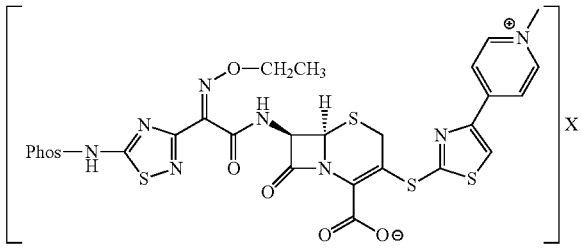

wherein

Phos is a phosphate group; and

X is a cation selected from the group consisting of an imidazolium cation which can be optionally substituted by one or more $C_{1-6}$ alkyl groups and a magnesium cation.

The compound having the formula (1) can be transformed into a compound having the formula (4)

(4)

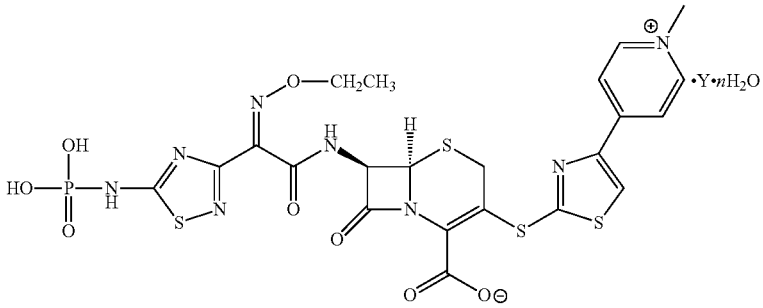

wherein Y is $CH_3COOH$, $CH_3CH_2COH$ or $CH_3CN$; and n is 0 to 5.

DETAILED DESCRIPTION

In one embodiment, the present invention relates to a compound having the formula (1)

(1)

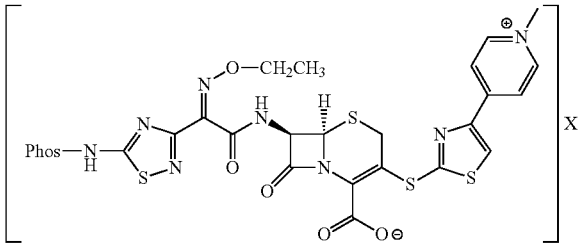

wherein

Phos is a phosphate group; and

X is a cation selected from the group consisting of an imidazolium cation which can be optionally substituted by one or more $C_{1-6}$ alkyl groups or a magnesium cation; as well as a pharmaceutically acceptable solvate thereof.

It is understood that the charge of the cation and the charge of the phosphate group will be chosen so that the compound having the general formula (1) will have a neutral net charge. For instance, if the cation is an imidazolium cation, then the phosphate group will typically be

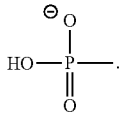

Whereas if the cation is a magnesium cation, then the phosphate group will typically be

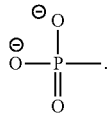

Therefore, preferred compounds according to the present invention include

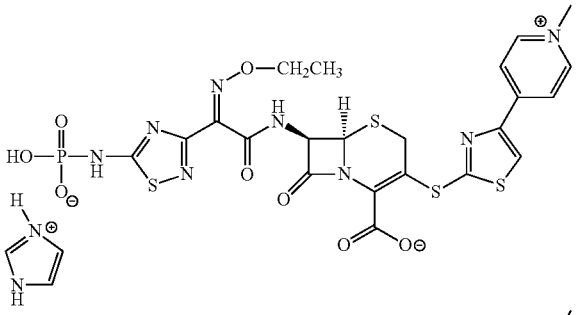

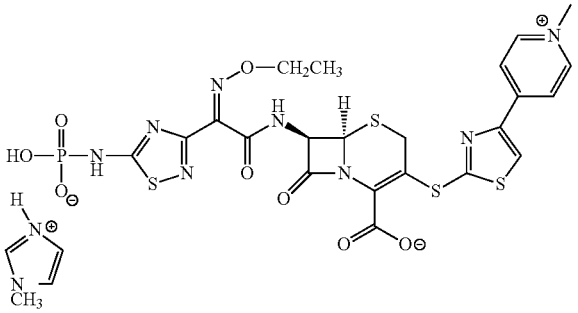

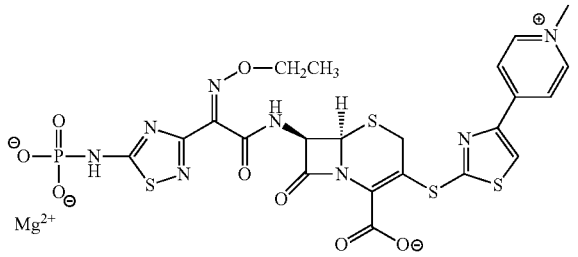

In the second formula only one of the possible imidazolium cations which are substituted by one or more $C_{1-6}$ alkyl groups is shown. It is to be understood that the present invention does not only cover the 1-methylimidazole cation which is shown but also the 2-methylimidazole cation, 3-methylimidazole cation, 4-methylimidazole cation and 5-methylimidazole cation as well as respective imidazole cations having more than one methyl group. Furthermore, the present invention is not restricted to methyl as a $C_{1-6}$ alkyl group but also covers corresponding cations in which the imidazolium cation is substituted by other straight or branched $C_{1-6}$ alkyl groups including ethyl, propyl, butyl, pentyl and hexyl. Ethyl and methyl are preferred and methyl is more preferred. The number of substituents is not particularly limited and can be, e.g., 1 to 5, preferably 1 or 2, more preferably 1 $C_{1-6}$ alkyl group.

The compounds of the present invention can be provided in the form of a pharmaceutically acceptable solvate. The scope of the present invention embraces the compounds in any solvated form, including, e.g., solvates with water, for example hydrates, or with organic solvents such as methanol, ethanol, isopropanol or acetonitrile or with $C_{1-4}$ alkanoic acids such as acetic acid and propionic acid.

The present invention refers to a process comprising the steps of:

(i) reacting a compound having the formula (2) or a salt thereof (2)

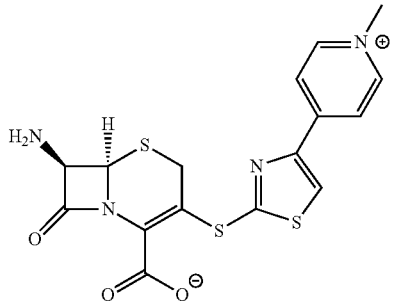

with a compound having the formula (3)

(3)

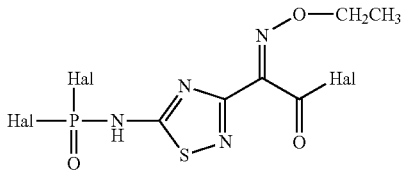

wherein Hal is a halogen; and (ii) adding a reagent selected from the group consisting of a magnesium salt, and an imidazole which can be optionally substituted by one or more $C_{1-6}$ alkyl groups;

to provide a compound having the formula (1)

(1)

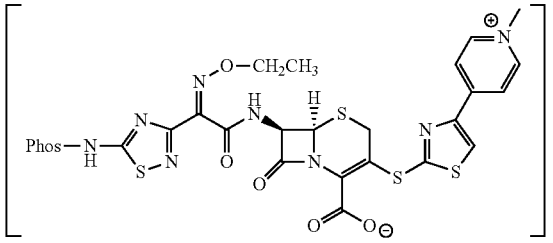

The compound having the formula (2) and the compound having the formula (3) are known in the art and can be prepared, e.g., as described in EP-A-1 310 502 or PCT/EP2012/067550.

The conditions for reacting the compound having the formula (2) and the compound having the formula (3) are not particularly restricted and any known reaction conditions can be chosen. In one possible embodiment, the compound having the formula (2) is first silylated and subsequently acylated. In an alternative embodiment, the compound having the formula (2) and the compound having the formula (3) are directly acylated.

In a preferred embodiment the ratio of the compound having the formula (2) to the compound having the formula (3) is in the range of about (1 to 3 mol):about (1 mol), preferably about (1 to 1.2 mol):about (1 mol).

The reaction will be typically conducted at about −40° C. to about 40° C., preferably about −10° C. to about 10° C.

The reaction duration is not particularly limited and can be, for instance, about 5 min to about 24 h, more preferably about 20 min to about 2 h.

If the direct acylation is chosen, the reaction preferably takes place in the presence of an acid scavenger which captures the acid that is generated during the reaction. Examples of suitable acid scavengers include salts (e.g., sodium hydrogen carbonate, sodium carbonate, potassium carbonate, sodium acetate, potassium acetate, and sodium phosphate), tertiary amines (e.g., triethylamine, tripropylamine, tributylamine, ethyldiisopropylamine, pyridine, lutidine, N,N-dimethylaniline, N-methylpiperidine, N-methylpyrrolidine, and N-methylmorpholine), alkylene oxides (e.g., propyleneoxide, and epichlorohydrin) and mixtures thereof. Of these, a combination of sodium hydrogen carbonate, sodium carbonate, sodium acetate, triethylamine or sodium acetate with triethylamine is preferable, and particularly a combination of sodium hydrogen carbonate, sodium acetate, triethylamine or sodium acetate with triethylamine is more preferable. In this embodiment the solvent is usually any suitable solvent that does not detrimentally effect the reaction. Examples of possible solvents include solvents such as water, dimethylformamide, sulfolane, tetrahydrofran and mixtures thereof can be used.

In the alternative embodiment in which a silylation is conducted a silane is used. The silane is not particularly restricted and can, for example, be a silane having the formula $HalSiR_3$ (wherein Hal is a halogen; preferably Cl, Br, or I; more preferably I; and R is independently selected from a $C_{1-6}$ alkyl group; preferably $CH_3$); a silazane having the formula $R_3Si—NH—SiR_3$ (wherein R is independently selected from a $C_{1-6}$ alkyl group; preferably $CH_3$), a silylurea compound having the formula $R_3Si—NH—C(O)—NH—SiR_3$ (wherein R is independently selected from a alkyl group; preferably $CH_3$), a silylformamide having the formula $H—C(O)—N(SiR_3)_2$ (wherein R is independently selected from a $C_{1-6}$ alkyl group; preferably $CH_3$), or a silylacetamide having the formula $R_3Si—N=C(CH_3)—O—SiR_3$ or $R_3Si—N=C(CF_3)—O—SiR_3$ (wherein R is independently selected from a $C_{1-6}$ alkyl group; preferably $CH_3$). The silane silylates the carboxylic acid group of the compound having the formula (2). Examples of possible silanes include N,O-bistrimethylsilylacetamide, trimethylsilylacetamide, bistrimethylsilylformamide, bistrimethylsilyltrifluoroacetamide, N,N'-bistrimethylsilylurea, trimethylsilyliodide, hexamethyldisilazane and mixtures thereof.

The silylation reaction is typically conducted in a polar solvent such as a nitrile solvent (including acetonitrile) or an amide solvent (including dimethylacetamide). The reaction temperature is not particularly limited and can be, for instance, in the range of about −40° C. to about 40° C., preferably about −10° C. to about 30° C.

The silylated intermediate having the formula (5) can then be reacted with the compound having the formula (3). The reaction is usually carried out in the same solvent which was employed in the silylation reaction. The reaction temperature is not particularly limited and can be chosen, e.g., in the range of about −10° C. to about 10° C. An acid scavenger is typically not required if a silylated intermediate is reacted with the compound having the formula (3). After this reaction the silyl group $—SiR_3$ is usually removed by hydrolysis. The hydrolysis reaction can be conducted with or without the presence of an acid scavenger. Examples of suitable acid scavengers include salts (e.g., sodium hydrogen carbonate, sodium acetate, magnesium acetate), tertiary amines (e.g., triethylamine, tripropylamine, tributylamine, ethyldiisopropylamine, pyridine, lutidine, N,N-dimethylaniline. N-methylpiperidine, N-methylpyrrolidine, and N-methylmorpholine), Amberlite LA 2 (N-dodecyl-N-isododecylamine), alkylene oxides (e.g., propylene oxide, and epichlorohydrin) and mixtures thereof.

After the acylation, a reagent selected from the group consisting of a magnesium salt and an imidazole which can be optionally substituted by one or more $C_{1-6}$ alkyl groups is added to provide a compound having the formula (1)

(1)

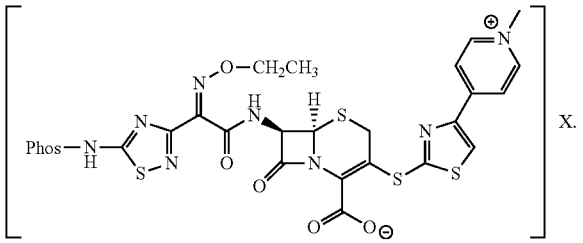

In the embodiment in which a magnesium salt of the compounds of the present invention is to be prepared, it is also possible to use a magnesium salt as an acid scavenger and to thus prepare the compounds of the present invention in situ.

The magnesium salt is not particularly restricted and can, for example, be selected from the group consisting of magnesium salts of carboxylic acids such as magnesium acetate, magnesium formiate, magnesium lactate, magnesium aspartate and magnesium citrate; magnesium salts of sulfonic acids such as magnesium methanesulfonate which can, for example, be used in combination with a tertiary amine (e.g., a $C_{1-4}$ alkyl amine like tributylamine); as well as inorganic magnesium salts such as magnesium chloride which can, for example, be used in combination with a tertiary amine (e.g., a $C_{1-4}$ alkyl amine like tributylamine). Hydrates of these magnesium salts are also possible.

The ratio of the magnesium salt to the compound having the formula (3) is preferably about (1 to 6 mol):(1 mol), more preferably about (1.1 to 3 mol):(1 mol).

The reaction can be conducted in any suitable solvent that does not detrimentally effect the reaction. Examples of possible solvents include polar solvents such as alcohols (such as $C_{1-4}$ alcohols), nitriles (such as acetonitrile), alcohols (such as ethanol, isopropanol), ethers (such as tetrahydrofuran), amides (such as dimethylformamide, dimethylacetamide), ketones (such as acetone) and esters (such as ethyl acetate). Mixtures of these solvents can also be used.

The reaction will be typically conducted at about −40° C. to about 40° C., preferably about −30° C. to about −10° C.

The reaction duration is not particularly limited and can be, for instance, about 30 min to about 24 h, more preferably about 30 min to about 4 h.

In an alternative embodiment, the reagent is an imidazole which can be optionally substituted by one or more $C_{1-6}$ alkyl groups. Examples thereof include imidazole and methyl-imidazole.

The ratio of the imidazole which can be optionally substituted by one or more $C_{1-6}$ alkyl groups to the compound having the formula (3) is preferably about (1 to 10 mol):(1 mol), more preferably about (1.5 to 8 mol):(1 mol).

The reaction can be conducted in any suitable solvent that does not detrimentally effect the reaction. Examples of possible solvents include polar solvents such as alcohols (such as $C_{1-4}$ alcohols), nitriles (such as acetonitrile), ethers (such as tetrahydrofuran), amides (such as dimethylformamide, dimethylacetamide), ketones (such as acetone) and esters (such as ethyl acetate). Mixtures of these solvents can also be used.

The reaction will be typically conducted at about −40° C. to about 40° C., preferably about −10° C. to about 10° C.

The reaction duration is not particularly limited and can be, for instance, about 10 min to about 24 h, more preferably about 30 min to about 4 h.

The compound having the formula (1) can be crystallized and isolated from the reaction mixture. If desired, it can be isolated and, for example, washed and dried before it is subjected to further processing.

If desired, the compound having the formula (1) can be transformed into a compound having the formula (4)

(4)

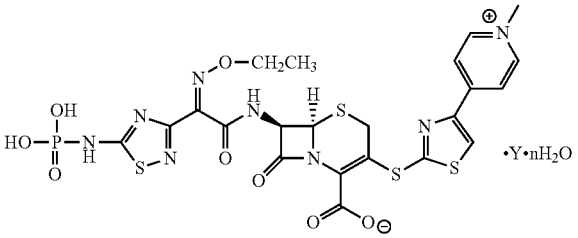

Y is preferably $CH_3COOH$, $CH_3CH_2COOH$ or $CH_3CN$, more preferably $CH_3COOH$.

n is 0 to 5.

This transformation reaction is not particularly limited and any reaction previously employed with respect to the corresponding compounds in which X is a sodium cation can be employed. In one embodiment, the transformation reaction can be conducted by adding an acid. Examples of acids include inorganic acids (such as sulfuric acid, phosphoric acid, and hydrochloric acid) as well as organic acids (such as 4-toluenesulfonic acid, methanesulfonic acid and oxalic acid). The pH of the reaction mixture is, for example, in the range of about 2 to about 0.5, preferably about 0.8 to about 0.6.

The transformation can be conducted, e.g., at a temperature in the range of about 0° C. to about 40° C., preferably about 0° C. to about 30° C.

The solvent is not particularly limited and can be a polar solvent such as water, carboxylic acids (such as acetic acid) and nitrile solvents (such as acetonitrile). As well as mixtures thereof.

The desired product can be obtained by removing the solvent. The procedures for solvent removal are well known in the art and include evaporation as well as crystallization from the solution. In a preferred embodiment the solvent is removed by crystallizing in a mixture of water and acetic acid. The acid which is formed in the reaction between the compound having the formula (1) and the compound having the formula (2) can be neutralized, for example, by a base such as a tri($C_{1-4}$alkyl)amine like triethylamine or ethyldiisopropylamine. If an imidazolium salt is to be prepared, it is possible to use the imidazole itself as a base for neutralizing the acid. If the magnesium salt is to be prepared, it is possible to use a magnesium acetate as a base for neutralizing the acid. The compounds having the formula (1) are soluble in water. If water is used as a solvent or for the hydrolysis, an anti-solvent, e.g. acetonitrile, isopropanol or tetrahydrofuran, can be used to improve the crystallization and isolation of the compound having the formula (1).

Previously, for example in EP-A-1 310 502 and EP-A-1 043 327, a compound having the formula (1) in which X was sodium was used as an intermediate. This sodium compound was instable and degraded during processing, so that by-products were formed which had to be removed, e.g., by column chromatography. The present inventors have surprisingly found that the compound having the formula (4) can be provided in the same purity level without having to conduct column chromatography if X is a cation selected from the group consisting of imidazolium cation which can be optionally substituted by one or more $C_{1-6}$ alkyl groups and a magnesium cation. Without wishing to be bound by theory, it is assumed that the compounds of the present invention, particularly the imidazolium compounds, are more stable than the known ceftaroline disodium salt. Therefore, the present process can be conducted without having to use column chromatography, or preferably other purification steps such as any type of chromatography.

Typically, the HPLC-purity of the ceftaroline fosamil via imidazolium salt is up to 97.6 area %.

The present invention is illustrated by the following non-limiting examples.

EXAMPLES

Example 1

4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, magnesium salt To a mixture of 300 mL acetonitrile and 30 mL dimethylacetamide was added 15.0 g of 4-[2-[[(6R,7R)-7-amino-2-carboxy-8-oxo-5-thia-1-azabicyclo[4.2.0]oct-2-en-3-yl]thio]-4-thiazolyl]-1-methyl-pyridinium, chloride, hydrochloride (31.3 mmol) and 22.8 g of N,O-bistrimethylsilylacetamide (3.6 equi, 112 mmol). After stirring for 45 minutes the resulting solution was cooled to 0° C. At this temperature 11.25 g of 2-(5-(dichlorophosphinyl)amino]-1,2,4-thiadiazole-3-yl]-2(Z)-ethoxyiminoacetyl chloride (1.02 equi, 32.0 mmol) was added and stirring was continued for 30 minutes. Then the reaction mixture was poured into 300 mL of ice water and stirred for 1 hour at 0° C. To the mixture was added 300 mL of tetrahydrofuran (THF). After stirring for 16 hours at 0° C., 3.0 g of charcoal was added and after 5 minutes stirring charcoal was removed by filtration. The pH of the filtrate was adjusted to 3.0 by adding approx. 62 g of Amberlite LA 2 (N-dodecyl-N-isododecylamine). To the mixture was added 300 mL of heptane. After 5 minutes stirring the layers were separated and the organic layer was discarded. The aqueous layer was extracted once more with 150 mL of heptane. To the extracted aqueous layer were added 8.25 g of magnesium acetate tetrahydrate (1.2 equi, 38.5 mmol) and 300 mL acetonitrile. After stirring for 30 minutes at ambient temperature the suspension was cooled to 0° C. and stirred at this temperature for 1 hour. The crystals were isolated by filtration, washed with 90 mL aqueous acetonitrile (1/1) and 270 mL of acetonitrile. After drying in vacuo at room temperature 21.3 g of ceftaroline fosamil magnesium salt were obtained in the form of a crystalline powder.

mp: 250° C. (dec.)

Example 2

4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, imidazolium salt To a mixture of 300 mL acetonitrile and 30 mL dimethylacetamide were added 15.0 g of 4-[2-[[(6R,7R)-7-amino-2-carboxy-8-oxo-5-thia-1-azabicyclo[4.2.0]oct-2-en-3-yl]thio]-4-thiazolyl]-1-methyl-pyridinium, chloride, hydrochloride (31.3 mmol) and 22.8 g of N,O-bistrimethylsilylacetamide (3.6 equi, 112 mmol). After stirring for 45 minutes the resulting solution was cooled to 0° C. At this temperature 11.25 g of 2-(5-(dichlorophosphinyl)amino]-1,2,4-thiadiazole-3-yl]-2(Z)-ethoxyiminoacetyl chloride (1.02 equi, 32.0 mmol) was added and stirring was continued for 30 minutes. Then the reaction mixture was poured into 300 mL of ice water. To the solution were added 150 mL of tetrahydrofuran. After stirring for 16 hours at 0° C. to the mixture were added 3.0 g of charcoal and after 5 minutes stirring the charcoal was removed by filtration. To the filtrate were added 15.0 g of imidazole (7.0 equi, 220 mmol) and then 450 mL of ethanol were added dropwise over 30 minutes. The resulting slurry was stirred for 2 hours at 0° C. The crystals were isolated by filtration and washed with 200 mL of ethanol. After drying in vacuo at room temperature 17.6 g (74.8%) of the imidazolium salt were obtained in the form of a crystalline powder.

mp: 184° C.

Example 3

4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, 1-methylimidazolium salt To a mixture of 300 mL acetonitrile and 30 mL dimethylacetamide were added 15.0 g of 4-[2-[[(6R,7R)-7-amino-2-carboxy-8-oxo-5-thia-1-azabicyclo[4.2.0]oct-2-en-3-yl]thio]-4-thiazolyl]-1-methyl-pyridinium, chloride, hydrochloride (31.3 mmol) and 22.8 g of N,O-bistrimethylsilylacetamide (3.6 equi, 112 mmol). After stirring for 45 minutes the resulting solution was cooled to 0° C. At this temperature 11.25 g of 2-(5-(dichlorophosphinyl)amino]-1,2,4-thiadiazole-3-yl]-2(Z)-ethoxyiminoacetyl chloride (1.02 equi, 32.0 mmol) was added and stirring was continued for 30 minutes. Then the reaction mixture was poured into 300 mL of ice water and stirred for 16 hours at 0° C. To the mixture were added 3.0 g of charcoal and after 5 minutes stirring charcoal was removed by filtration. To the filtrate were added 18.0 g of 1-methyl-imidazole (7.0 equi, 219 mmol) and then 900 mL of isopropanol were added dropwise over 30 minutes. The resulting slurry was stirred for 2 hours at 0° C. The crystals were isolated by filtration and washed with 300 mL of isopropanol. After drying in vacuo at room temperature 16.8 g (70.1%) of the 1-methylimidazolium salt were obtained in the form of a crystalline powder.

mp: 199° C.

Example 4

4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, magnesium salt To 24 ml deionized water was added 4.0 g of 4-[2-[[(6R,7R)-7-amino-2-carboxy-8-oxo-5-thia-1-azabicyclo[4.2.0]oct-2-en-3-yl]thio]-4-thiazolyl]-1-methyl-pyridinium, chloride, hydrochloride (8.3 mmol). The suspension was cooled to 10° C. At this temperature 5.5 mL of 3M sodium acetate were added and the pH of the mixture is adjusted to 8.5 by addition of approx. 2.3 mL of triethylamine. The resulting solution was cooled to 0° C. At this temperature 5 mL of triethylamine and a cold (−40° C.) solution of 3.5 g of 2-(5-(dichlorophosphinyl)amino]-1,2,4-thiadiazole-3-yl]-2(Z)-ethoxyiminoacetyl chloride (1.02 equi, 32.0 mmol) in 9.5 mL of tetrahydrofuran were added thereto immediately. Then the reaction mixture was warmed to 22° C. and stirred at this temperature for 1 hour while keeping the pH to 5.0 by adding approx. 1.1 mL of triethylamine. After stirring for 1 hour 1.78 g of magnesium acetate tetrahydrate (1.0 equi, 8.3 mmol) were added. To the mixture were added 92 mL of ethanol. The resulting suspension was cooled to 0° C. and stirred at this temperature for 1 hour. The crystals were isolated by filtration. The cake was washed with 20 mL of cooled ethanol/water (2/1), 40 mL of cooled ethanol and 40 mL of methyl t-butyl ether. The wet product was dried at ≤20° C. in vacuo yielding 5.98 g of a crystalline powder.

mp: 250° C. (dec.)

Example 5

4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, acetic acid solvate monohydrate To a solution of 2.6 g of D-mannitol in 36.7 g of water and 47.8 g of acetic acid were added 16.0 g of 4-[2-[[(6R,7R)-2-carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, magnesium salt (22.6 mmol). To the slurry were added 7.6 mL of 2.5M sulfuric acid and 0.8 g of charcoal. After 5 minutes stirring charcoal was removed by filtration. The charcoal was washed with 5 mL of acetic acid/water (1/1). Filtrate and wash liquid were combined, seeds were added and the mixture was stirred at room temperature for 2 hours. The suspension was cooled to 0° C. and stirred for 2 hours at this temperature. Then the crystals were isolated by filtration, washed with 25 mL of acetic acid/water/1/1), 25 mL acetic acid/water (1/4) and 25 mL of ethanol/acetic acid (1/1), and dried in vacuo give 7.5 g of the title compound.

1H NMR (DMSO-d6): d 1.24 (3H, t, J=7 Hz), 1.91 (3H, s), 3.58, 3.95 (2H, ABq, J=17 Hz), 4.17 (2H, q, J=7 Hz), 4.34 (3H, s), 5.32 (1H, d, J=5 Hz), 5.92 (1H, dd, J=5 Hz, 8 Hz), 8.51 (2H, d, J=6 Hz), 8.99 (3H, m), 9.30 (1H, m), 9.70 (1H, d, J=8 Hz)

Example 6

4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, acetonitrile solvate To 249 mL of water and 270 mL of acetonitrile were added 36.5 g of 4-[2-[[(6R,7R)-2-carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methyl-pyridinium, inner salt, magnesium salt (51.6 mmol). To the solution were added at room temperature 7.1 mL acetic acid, 21.6 mL of conc. hydrochloric acid and 2.2 g of charcoal. After 5 minutes stirring the charcoal was removed by filtration. The charcoal was washed with 40 mL of acetonitrile/water (5/2). Filtrate and wash liquid were combined and 274 mL of acetonitrile were added dropwise over 30 minutes at room temperature. The suspension was cooled to 0° C. and stirred for 1 hour at this temperature. Then the crystals were isolated by filtration, washed with 25 mL of acetonitrile/water (2/1) and 50 mL of acetonitrile, and dried in vacuo to give 14.5 g of the title compound.

1H NMR (DMSO-d6): d 1.23 (3H, t, J=7 Hz), 2.07 (3H, s), 3.58, 3.95 (2H, ABq, J=17 Hz), 4.17 (2H, q, J=7 Hz), 4.33 (3H, s), 5.32 (1H, d, J=5 Hz), 5.91 (1H, dd, J=5 Hz, 8 Hz), 8.51 (2H, d, J=6 Hz), 8.99 (3H, m), 9.34 (1H, m), 9.71 (1H, d, J=8 Hz)

Example 7

4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, acetic acid solvate monohydrate To 88 ml of water and 154 ml of acetic acid were added 38.0 g of 4-[2-[[(6R,7R)-2-carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methyl-pyridinium, inner salt, imidazolium salt. To the resulting solution were added 3 g of charcoal. After 5 minutes stirring charcoal was removed by filtration. The charcoal was washed with 20 mL of water. Filtrate and wash liquid were combined and after addition of 15.7 mL of 2.5M sulfuric acid and seeds the mixture was stirred at room temperature for 2 hours. The suspension was cooled to 0° C. and stirred for 2 hours at this temperature. Then the crystals were isolated by filtration, washed with 290 mL of acetic acid/water (1/1), 150 mL acetic acid/water (1/4) and 150 mL of ethanol/acetic acid (1/1), and dried in vacuo to give 24.3 g of the title compound.

1H NMR (DMSO-d6): d 1.24 (3H, t, J=7 Hz), 1.91 (3H, s), 3.58, 3.95 (2H, ABq, J=17 Hz), 4.17 (2H, q, J=7 Hz), 4.34 (3H, s), 5.32 (1H, d, J=5 Hz), 5.92 (1H, dd, J=5 Hz, 8 Hz), 8.51 (2H, d, J=6 Hz), 8.99 (3H, m), 9.30 (1H, m), 9.70 (1H, d, J=8 Hz)

Comparative Example 1

4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, inner salt, disodium salt 4-[2-[[(6R,7R)-2-Carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methyl-pyridinium, inner salt, disodium salt was prepared according to the method described in Working Example 1 of EP 1 043 327 B1. HPLC-analysis of the isolated disodium salt showed formation of by-products during the drying process and storage at 20° C. This indicates that the isolated disodium salt was very unstable.

The starting materials 2-(5-(dichlorophosphinyl)amino]-1,2,4-thiadiazole-3-yl]-2(Z)-ethoxyiminoacetyl chloride and 4-[2-[[(6R,7R)-7-amino-2-carboxy-8-oxo-5-thia-1-azabicyclo[4.2.0]oct-2-en-3-yl]thio]-4-thiazolyl]-1-methyl-pyridinium, chloride, hydrochloride monohydrate were prepared according to the procedures described in EP-A-1 310 502.

The invention claimed is:

1. A compound having the formula (1)

(1)

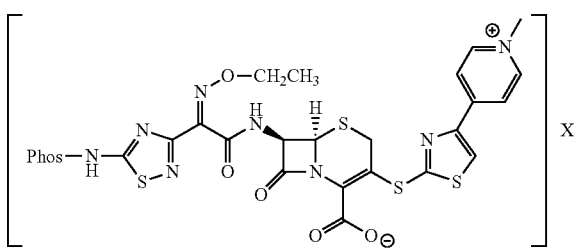

wherein

Phos is a phosphate group; and

X is a cation selected from the group consisting of a magnesium cation and an imidazolium cation which can be optionally substituted by one or more $C_{1-6}$ alkyl groups; as well as a pharmaceutically acceptable solvate thereof selected from an acetic acid solvate or an acetonitrile solvate.

2. The compound according to claim 1, wherein X is an imidazolium cation which can be optionally substituted by one or more $C_{1-6}$ alkyl groups.

3. The compound according to claim 2, wherein X is an imidazolium cation or a methyl-imidazolium cation.

4. The compound according to claim 1, wherein X is a magnesium cation.

5. A process comprising the steps of:

(i) reacting a compound having the formula (2) or a salt thereof (2)

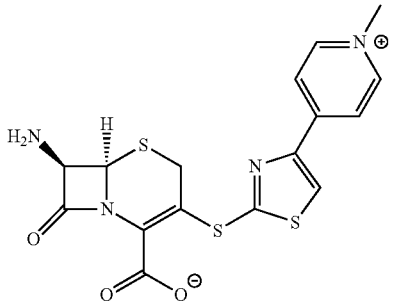

with a compound having the formula (3)

(3)

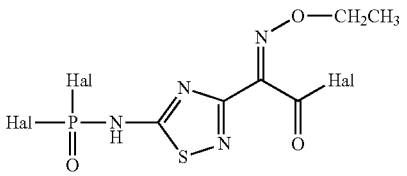

wherein Hal is a halogen; and (ii) adding a reagent selected from the group consisting of a magnesium salt and an imidazole which can be optionally substituted by one or more $C_{1-6}$ alkyl groups; to provide a compound having the formula (1)

(1)

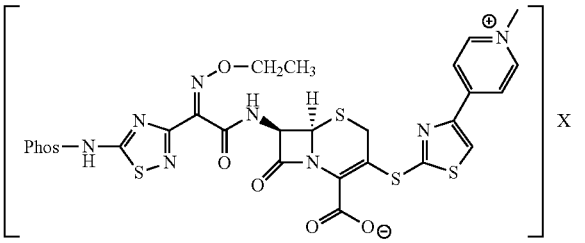

wherein

Phos is a phosphate group; and

X is a cation selected from the group consisting of a magnesium cation and an imidazolium cation which can be optionally substituted by one or more $C_{1-6}$ alkyl groups.

6. A process comprising the steps of:

(a) reacting a compound having the formula (2) or a salt thereof (2)

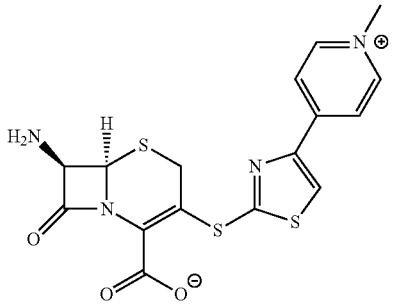

with a silane to provide a compound having the formula (5)

(5)

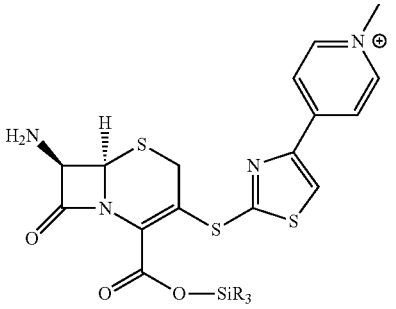

wherein R is independently selected from a $C_{1-6}$ alkyl group;

(b) reacting the compound having the formula (5) with a compound having the formula (3)

(3)

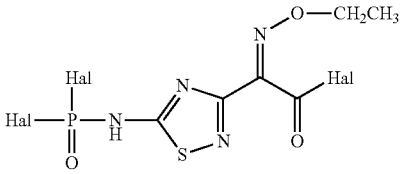

wherein Hal is a halogen;

(c) removing the silyl group —$SiR_3$ from the resultant compound; and (d) adding a reagent selected from the group consisting of a magnesium salt and an imidazole which can be optionally substituted by one or more $C_{1-6}$ alkyl groups; to provide a compound having the formula (1)

(1)

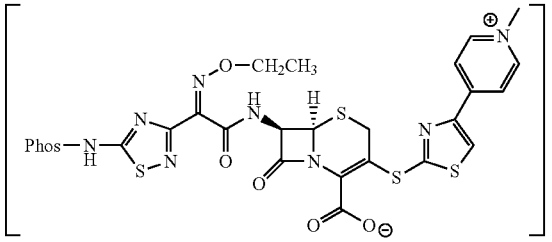

wherein

Phos is a phosphate group; and

X is a cation selected from the group consisting of a magnesium cation and an imidazolium cation which can be optionally substituted by one or more $C_{1-6}$ alkyl groups.

7. The process according to claim 5, wherein the magnesium salt is selected from the group consisting of magnesium acetate as well as hydrates thereof.

8. The process according to claim 5, wherein the compound having the formula (1) is transformed into a compound having the formula (4)

(4)

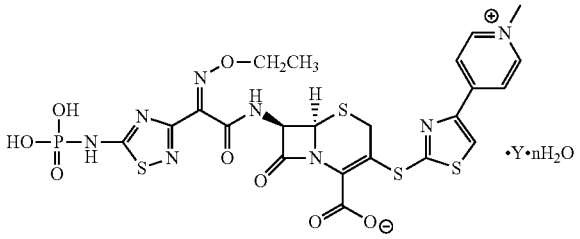

wherein Y is $CH_3COOH$, $CH_3CH_2COOH$ or $CH_3CN$; and n is 0 to 5.

9. The process according to claim 6, wherein the magnesium salt is selected from the group consisting of magnesium acetate as well as hydrates thereof.

10. The process according to claim 6, wherein the compound having the formula (1) is transformed into a compound having the formula (4)

(4)

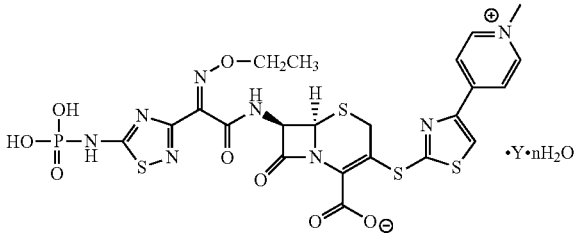

wherein Y is $CH_3COOH$, $CH_3CH_2COOH$ or $CH_3CN$; and n is 0 to 5.

11. The compound according to claim 1, wherein the compound is an acetic acid solvate or acetonitrile solvate.

*12. A process comprising the step of transforming a compound having the formula (1)*

*(1)*

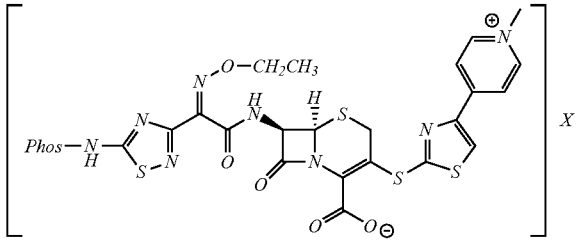

*wherein*

*Phos is a phosphate group; and*

*X is a cation selected from the group consisting of a magnesium cation and an imidazolium cation which can be optionally substituted by one or more $C_{1-6}$ alkyl groups;*

*into a compound having the formula (4)*

*(4)*

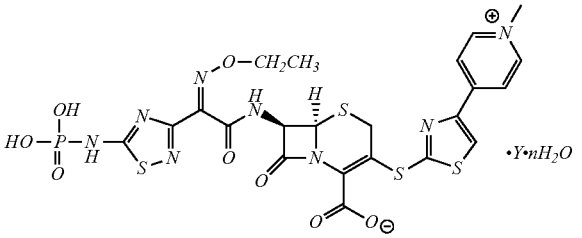

*wherein Y is $CH_3COOH$, $CH_3CH_2COOH$ or $CH_3CN$; and n is 0 to 5.*

* * * * *